United States Patent
Chen et al.

(10) Patent No.: US 12,364,667 B2
(45) Date of Patent: Jul. 22, 2025

(54) ANTI-TUMOR PLATINUM-BASED DRUG MINERALIZED PROTEIN NANOPARTICLE, PREPARATION METHOD THEREFOR AND USE THEREOF

(71) Applicant: SOOCHOW UNIVERSITY, Suzhou (CN)

(72) Inventors: Huabing Chen, Suzhou (CN); Yibin Deng, Suzhou (CN); Hong Yang, Suzhou (CN); Hengte Ke, Suzhou (CN); Ling Liu, Suzhou (CN); Ting Li, Suzhou (CN); Tao Yang, Suzhou (CN); Lu Wang, Suzhou (CN)

(73) Assignee: SOOCHOW UNIVERSITY, Suzhou (CN)

( * ) Notice: Subject to any disclaimer, the term of this patent is extended or adjusted under 35 U.S.C. 154(b) by 750 days.

(21) Appl. No.: 17/560,155

(22) Filed: Dec. 22, 2021

(65) Prior Publication Data

US 2022/0110883 A1    Apr. 14, 2022

Related U.S. Application Data

(63) Continuation of application No. PCT/CN2019/102652, filed on Aug. 26, 2019.

(51) Int. Cl.
*A61K 9/51* (2006.01)
*A61K 31/282* (2006.01)
*A61K 33/243* (2019.01)

(52) U.S. Cl.
CPC .......... *A61K 9/5169* (2013.01); *A61K 9/5192* (2013.01); *A61K 31/282* (2013.01); *A61K 33/243* (2019.01)

(58) Field of Classification Search
CPC .. A61K 9/5169; A61K 33/243; A61K 9/5192; A61K 31/282
See application file for complete search history.

(56) References Cited

U.S. PATENT DOCUMENTS

2022/0054424 A1*  2/2022  Lollo ................... A61K 31/282

FOREIGN PATENT DOCUMENTS

| CN | 109730998 A | 5/2019 |
|----|-------------|--------|
| CN | 110368374 A | 10/2019 |

* cited by examiner

*Primary Examiner* — Robert A Wax
*Assistant Examiner* — Olga V. Tcherkasskaya
(74) *Attorney, Agent, or Firm* — SZDC Law PC

(57) ABSTRACT

Anti-tumor platinum drug mineralized protein nanoparticles and a preparation method therefor are disclosed. The anti-tumor platinum-based drug mineralized protein nanoparticles include a platinum drug and a protein. The protein is one or more selected from the group consisting of albumin, transferrin, hemoglobin, and low-density lipoprotein. The platinum drug is cisplatin, iodoplatin, bromoplatin, oxaliplatin, carboplatin, or nedaplatin. A drug loading of the anti-tumor platinum-based drug mineralized protein nanoparticles is 1% to 50%.

7 Claims, 10 Drawing Sheets

ANTI-TUMOR PLATINUM-BASED DRUG MINERALIZED PROTEIN NANOPARTICLE, PREPARATION METHOD THEREFOR AND USE THEREOF

This application is a Continuation Application of PCT/CN2019/102652, filed on Aug. 26, 2019, which is incorporated by reference for all purposes as if fully set forth herein.

TECHNICAL FIELD

The invention relates to biomedicine technology, and specifically relates to platinum drug mineralized protein nanoparticles, and a preparation method and application thereof.

BACKGROUND TECHNIQUE

Platinum drugs are commonly used clinical anti-tumor chemotherapeutics with broad-spectrum anti-tumor effects. Platinum drugs also have many shortcomings, such as poor efficacy, large toxic side effects, poor targeting, and prone to tumor drug resistance. Nano drug carriers (such as polymer micelles, vesicles, etc.) can improve this. However, the commonly used platinum anti-tumor drugs (such as cisplatin and its derivatives) are difficult to be loaded with traditional nano-carriers due to poor water and oil solubility. They are loaded with chemical coupling or prodrug modification to achieve their loading in the carrier. However, these nano-drug carriers often have disadvantages, such as difficulty in effective loading, complex preparation processes, and the use of non-medicinal excipients. Their clinical application is obviously restricted (Chem. Rev, 2016, 116, 3436-3486). Long-term use of platinum-based drugs often results in drug resistance, and the main resistance mechanisms include multidrug resistance-related protein (MRP1) and other mediating drug efflux, DNA self-repair, and drug inactivation. Therefore, to solve the problems of large side effects, poor targeting, and strong drug resistance of platinum-based small molecule chemotherapeutic drugs is the key to improve the clinical efficacy of platinum drugs.

SUMMARY OF THE INVENTION

Technical Problems

The method for preparing inorganic nanocrystalline protein nanoparticles relies on the interaction of amino acid residues in protein molecules with metal ions and the generation of inorganic precipitation, which is difficult to directly use for the inclusion of platinum drugs, such as cisplatin, and lacks tumor targeting and the reverse of the resistance. In addition, platinum drugs are all non-ionic precious metal complexes, which cannot be reacted to synthesize nanoparticles in proteins, and are difficult to be carried by carriers, so they are all used in the form of complexes. Therefore, there is an urgent need to develop a new type of platinum drug protein nanoparticles with clinical application prospects and tumor-targeting to achieve tumor-targeted delivery of platinum drugs, to overcome the tendency of platinum drugs to develop drug resistance, and to improve the anti-tumor effect of platinum drugs.

Technical Solutions

In view of the related art, the purpose of the present invention is to provide platinum drug mineralized protein nanoparticles, and a preparation method and application thereof.

In order to achieve the purpose of this invention, the present invention adopts the following technical solutions:

A kind of anti-tumor platinum drug mineralized protein nanoparticles are disclosed. The anti-tumor platinum drug mineralized protein nanoparticles include a platinum drug and protein.

In the present invention, the anti-tumor platinum drug mineralized protein nanoparticles include a platinum drug and a protein; the obtained anti-tumor platinum drug mineralized protein nanoparticles have a drug loading amount of 1%-50%, and the drug loading amount is the mass of platinum drugs/(the mass of platinum drugs+the mass of protein) in the purified sample; the mineralization in the present invention is a formation reaction of the platinum drug and the protein. Nanoparticles have good cytotoxic effects and are not human. The $IC_{50}$ of the small cell lung cancer cell A549 is 6.9 µg/mL.

The present invention uses a protein as a molecular reactor. First, a platinum prodrug compound is prepared, and then is mixed with the protein to enter an internal cavity thereof; further, through a ligand exchange reaction with leaving group of the platinum drug, the platinum drug is contained in the cavity of the protein to achieve controllable growth and to obtain its mineralization, realizing the mineralization reaction of the platinum drug in the protein, thereby preparing platinum drug mineralized protein nanoparticles. The invention is different from traditional nano-carriers for encapsulating drugs, and effectively solves the problem that that platinum drugs are usually non-ionic noble metal complexes and cannot realize their reaction to synthesize nanoparticles in a protein-water cavity. The platinum drug mineralized protein nanoparticle provided by the invention has the characteristics of long circulation in the body and tumor targeting, promotes the accumulation of platinum drugs in tumor tissues and enters tumor cells, and can reverse tumor drug resistance.

The present invention provides a method for preparing the above-mentioned anti-tumor platinum drug mineralized protein nanoparticles, which includes the following steps:
(1) Reacting a platinum drug and a silver salt in water and removing a precipitate to obtain a platinum prodrug compound aqueous solution; then mixing the platinum prodrug compound aqueous solution and a protein aqueous solution to obtain a platinum prodrug compound and protein complex mixture;
(2) Adjusting a pH value of the platinum prodrug compound and protein complex mixture to 4-12, adding a ligand aqueous solution, purifying after a reaction is complete to obtain the platinum drug mineralized protein nanoparticles.

The anti-tumor platinum drug mineralized protein nanoparticles of the present invention can be made into injections, and further made into various semi-solid preparations, solid preparations and the like.

An anti-tumor platinum drug mineralized protein nanoparticles freeze-dried powder. A preparation method of the anti-tumor platinum drug mineralized protein nanoparticles freeze-dried powder includes the following steps:
(1) reacting a platinum drug and a silver salt in water and removing a precipitate to obtain a platinum prodrug compound aqueous solution; then mixing the platinum prodrug compound aqueous solution and an aqueous protein solution to obtain a platinum prodrug compound and protein complex mixture;
(2) adjusting a pH value of the platinum prodrug compound and protein complex mixture to 4-12, adding an aqueous ligand solution, purifying after a reaction is complete, and lyophilizing to obtain the anti-tumor platinum drug mineralized protein nanoparticles freeze-dried powder.

In the present invention, in step (1), a centrifugal separation is used to remove the precipitate, the platinum drug and the silver salt are reacted at 50-60° C. for 3 hours in the absence of light, reaction temperature is reduced to room temperature, and the reaction is continued for 10-12 hours; in step (2), the reaction temperature is 25-60° C., the reaction time is 0.5-24 hours, preferably 2-8 hours. The purification is a centrifugal treatment in an ultrafiltration tube. Preferably, the centrifugal separation is performed at a rotation speed of 8000-15000 rpm for 8-15 minutes; the rotation speed of the centrifugal treatment is 1500-3000 rpm.

In the present invention, a molar ratio of platinum drugs to the silver salt is (1-5):1; a molar ratio of the platinum prodrug compound to the protein is (20-200):1; and a molar ratio of the platinum prodrug compound to the ligand is 1:(1-16). A concentration of the protein aqueous solution is 5-25 mg/mL. Preferably, the molar ratio of the platinum drug to the silver salt is (2-4):1; the molar ratio of the platinum prodrug compound to the protein is (50-150):1, more preferably (80-120):1; and the molar ratio of the platinum prodrug compound to the ligand is 1:(2-8); the concentration of the protein aqueous solution is 10-20 mg/mL. The growth rate of mineralization and the size of nanoparticles can be controlled. A concentration of the platinum prodrug compound solution is 0.04 to 1.0 mol/L, preferably 0.08 to 0.6 mol/L.

In the present invention, the ligand is chloride, bromide, iodide, 1,1-cyclobutane dicarboxylate, glycolate, oxalate, carbonate or bicarbonate; and the silver salt is silver nitrate or silver sulfate.

In the present invention, a protective agent used for lyophilization is one or more seleced from the group consisting of mannitol, glucose, sucrose, lactose and the like.

In the present invention, the protein is one or more selected from the group consisting of albumin, transferrin, hemoglobin, and low-density lipoprotein; and the platinum drug is cisplatin, iodoplatin, bromoplatin, oxaliplatin, carbohydrate patinum or nidaplatin.

The invention discloses an application of the anti-tumor platinum drug mineralized protein nanoparticles or the anti-tumor platinum drug mineralized protein nanoparticles freeze-dried powder in the preparation of anti-tumor drugs.

In the present invention, the water used as the solvent is preferably deionized water.

In the present invention, the ligand can be introduced in the form of a compound, for example, potassium iodide being added to introduce iodide ions.

In the present invention, the pH value of the mixed solution is adjusted by the NaOH aqueous solution or the HCl solution, and the concentration of the NaOH aqueous solution or the HCl solution is preferably 0.2 M.

The platinum drug mineralized protein nanoparticles of the present invention can be made into injections for intravenous injection, and can be further freeze-dried to make freeze-dried powder injections.

The method of preparing the platinum-based drug mineralized protein nanoparticles of the present invention can be described as follows as an example:

(1) Synthesis of a platinum drug precursor compound and protein complex mixture: a platinum drug and silver nitrate are mixed in a certain proportion and reacted in water at 5060° C. in the dark. After reacting for 2-5 hours, the temperature is cooled to room temperature, and the reaction is continued for 6-12 hours. The reaction mixture is centrifuged to remove the silver chloride precipitate, the supernatant obtained is the platinum prodrug compound solution, and the prepared platinum prodrug compound solution is thoroughly mixed with an albumin solution to obtain a mixed solution;

(2) Synthesis of platinum-based drug mineralized protein nanoparticles: the pH of the mixed solution is adjusted to between 4 and 12 with 0.2 M NaOH solution or HCl solution, then a ligand solution is added. The mixture is heated in a water bath at a set temperature, and reacted for a certain period of time. The mixture is transferred to an ultrafiltration tube, centrifuging to remove free platinum drug precursor compounds etc., to obtain platinum-based drug mineralized protein nanoparticles.

The present invention provides an application of the platinum drug mineralized protein nanoparticles in the preparation of anti-tumor drugs, especially drug-resistant anti-tumor drugs.

Beneficial Effects

The present invention uses a two-step preparation method for the first time to successfully prepare platinum drug mineralized protein nanoparticles, and the prepared nanoparticles are uniformly dispersed in an aqueous solution; the nanoparticles have good tumor cytotoxicity and are effective against human non-small cell lung cancer cells A549, with $IC_{50}$ of 6.9 g/ml. In the present invention, the insoluble platinum drug stably enters the albumin water cavity as a precursor complex, and a leaving group of the platinum prodrug compound causes a ligand exchange reaction, creating the formation of platinum drug mineralization in the protein cavity. Therefore, nanoparticles are prepared, which solves the problem of poor solubility of platinum drugs and difficulty in effective coating. By changing synthesis conditions, such as molar ratio, reaction time, etc., the particle size, drug release behavior and other physical and chemical properties are controlled, thus obtaining controlled release drug properties and targeted platinum drug mineralized protein nanoparticles. Compared with other platinum-loaded drug nanoparticles, the platinum drug mineralized protein nanoparticles of the present invention have significant advantages in simple preparation process, uniform size, controllable particle size, good biocompatibility, and good water solubility. The characteristics of long circulation time in the blood and high tumor targeting have laid the foundation for efficient tumor treatment and drug-resistant tumor treatment.

EXAMPLES OF THE PRESENT INVENTION

Figure 1:
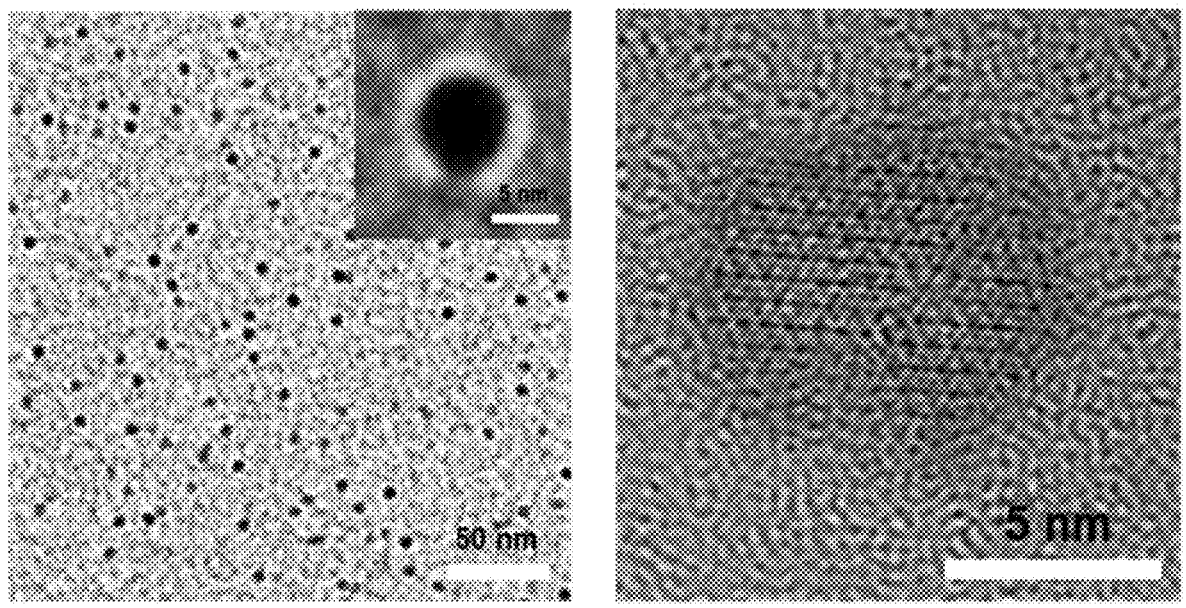
FIG. 1 is an electron micrograph of the iodoplatin protein nanoparticles of Example 1.

The specific implementation of the present invention will be described in further detail below in conjunction with the accompanying drawings and embodiments. The following examples are used to illustrate the present invention, but not to limit the scope of the present invention.

In the related art, the number of protein-binding platinum drugs, such as cisplatin or cisplatin derivatives, is very limited, and it is difficult to significantly improve the water solubility and tumor targeting effects and curative effects of cisplatin. In the present invention, proteins, such as albumin and transferrin, are A type of carrier material with good biocompatibility. Insoluble platinum drugs are stably entered into the albumin water cavity as precursor complexes, and platinum drug leaving groups cause ligand exchange reaction to induce platinum drug mineralization to be formed in the inner cavity of the protein, which solves the problem of poor solubility of platinum drugs and difficulty in effective coating. The preparation method of the platinum drug mineralized protein nanoparticles of the present invention is as follows:

(1) Reacting a platinum drug and a silver salt in water and removing a precipitate to obtain a platinum prodrug compound aqueous solution; then mixing the platinum prodrug compound aqueous solution and a protein aqueous solution to obtain a platinum prodrug compound and protein complex mixture;

(2) Adjusting a pH value of the platinum prodrug compound and protein complex mixture to 4-12, adding a ligand aqueous solution, purifying after a reaction is complete to obtain the platinum drug mineralized protein nanoparticles.

Example 1

The specific steps for preparing platinum drug mineralized protein nanoparticles are as follows:

Synthesis of platinum prodrug compound: After mixing cisplatin and silver nitrate in water at a molar ratio of 1:2, reacting for 3 hours at 60° C. in the dark, then cooling to room temperature, continuing the reaction for 10 hours, and then centrifuging the reaction mixture at a rotating speed 12000 rpm for 12 minutes to remove the silver chloride precipitate. The resulting supernatant is the platinum prodrug compound aqueous solution.

Taking 100 mM platinum prodrug compound aqueous solution and 13.3 mg/mL human serum albumin (HSA) aqueous solution and mixing thoroughly in a volume ratio of 1:5. A molar ratio of the platinum prodrug compound to the human serum albumin was 100:1. Adjusting the pH of the mixed solution to 6.4 with 0.2 M NaOH solution, and then adding potassium iodide (KI) aqueous solution to introduce the ligand ion, iodide ion, to obtain a mixed solution. A molar ratio of the platinum prodrug compound (diammine platinum ion dihydrate) and the ligand ion mole was 1:8. The mixture was heated at 55° C. for 4 hours, and the resulting mixture was then added to an ultrafiltration tube, centrifuging at 2000 rpm to remove impurities, such as iodide and potassium ions, to obtain iodoplatinum protein nanoparticles, which are platinum drug mineralized protein nanoparticles.

The above-mentioned iodoplatin protein nanoparticles were freeze-dried using mannitol as a protective agent to obtain iodoplatin protein nanoparticles freeze-dried powder. The conditions of the freeze-drying were: pre-freezing the sample at −80° C. for 10 hours, and then quickly transferring the sample to the cold trap, temperature lowered to −20° C. in the freeze dryer, the vacuum degree being at 10 Pa, and the drying being carried out for 12 hours, and then the temperature being gradually increased to 30° C., and the drying is continued for 2 hours.

The prepared iodoplatin protein nanoparticles were photographed by electron microscopy. The results are shown in FIG. 1. The prepared nanoparticles are uniformly dispersed and have uniform particle size. The average particle size (drug particle size) is 7.0=0.8 nm, and the drug loading is 25%.

Example 2

Figure 2:
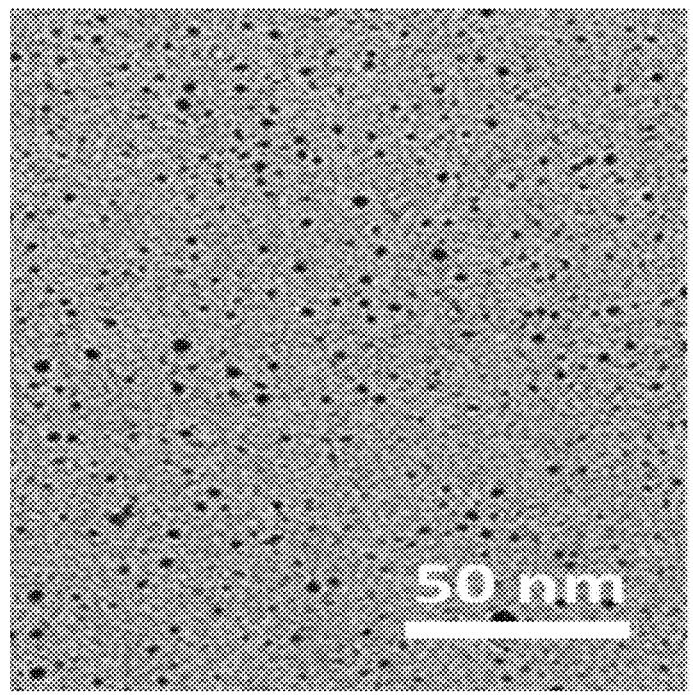
FIG. 2 is an electron micrograph of the iodoplatin protein nanoparticles of Example 2.

The steps in this example were the same as those in Example 1, except that the molar ratio of the platinum prodrug compound to the ligand ion was 1:4. The prepared nanoparticles were photographed by electron microscopy. The result is shown in FIG. 2. The average size of the nanoparticles is 4.1±0.3 nm.

Example 3

Figure 3:
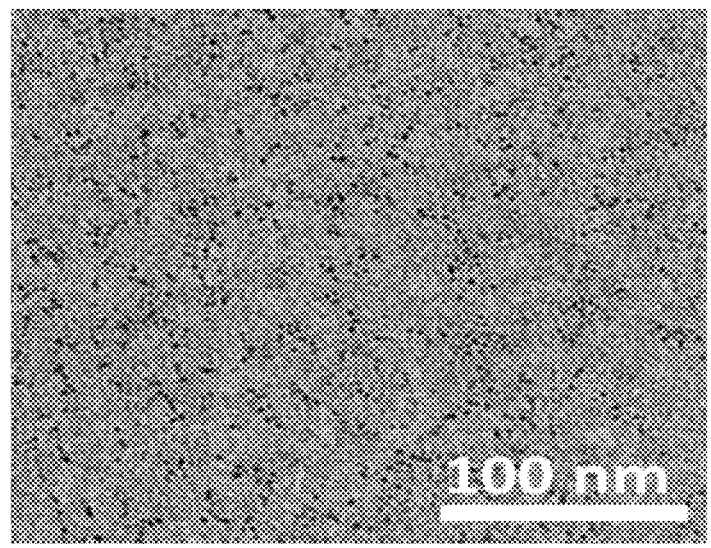
FIG. 3 is an electron micrograph of the iodoplatin protein nanoparticles of Example 3.

The steps of this example were the same as those of Example 1, except that the molar ratio of the platinum prodrug compound to the ligand ion is 1:2. The prepared nanoparticles were photographed by electron microscopy. The result is shown in FIG. 3. The average size of the nanoparticles is 2.3±0.2 nm.

Example 4

The steps in this example were the same as those of Example 1, except that the mixed solution was heated at 37° C. for 4 hours. The average particle size of the prepared nanoparticles is 1.8=0.4 nm.

Example 5

The steps in this example were the same as those of Example 1, except that the mixed solution was heated at 55° C. for 30 minutes. The average particle diameter of the prepared nanoparticles is 2.1±0.3 nm.

Example 6

The steps of this example were the same as those of Example 1, except that the reaction solution was heated at 55° C. for 2 hours. The prepared nanoparticles were photographed by electron microscope, and the average particle size of the prepared nanoparticles is 4.3±0.6 nm.

Example 7

The steps in this example were the same as those of Example 1, except that the concentration of the human serum albumin (HSA) solution was 20 mg/mL. The prepared nanoparticles were photographed by electron microscopy, the average particle size of the prepared nanoparticles is 4.8±0.5 nm and the drug loading is 19%.

Example 8

The steps in this example were the same as those of Example 1, except that the concentration of the platinum prodrug compound solution is 200 mM. The prepared nanoparticles were photographed by electron microscopy, and the average particle size of the prepared nanoparticles is 6.3±0.2 nm, and the drug load is 48%.

Example 9

Figure 4:
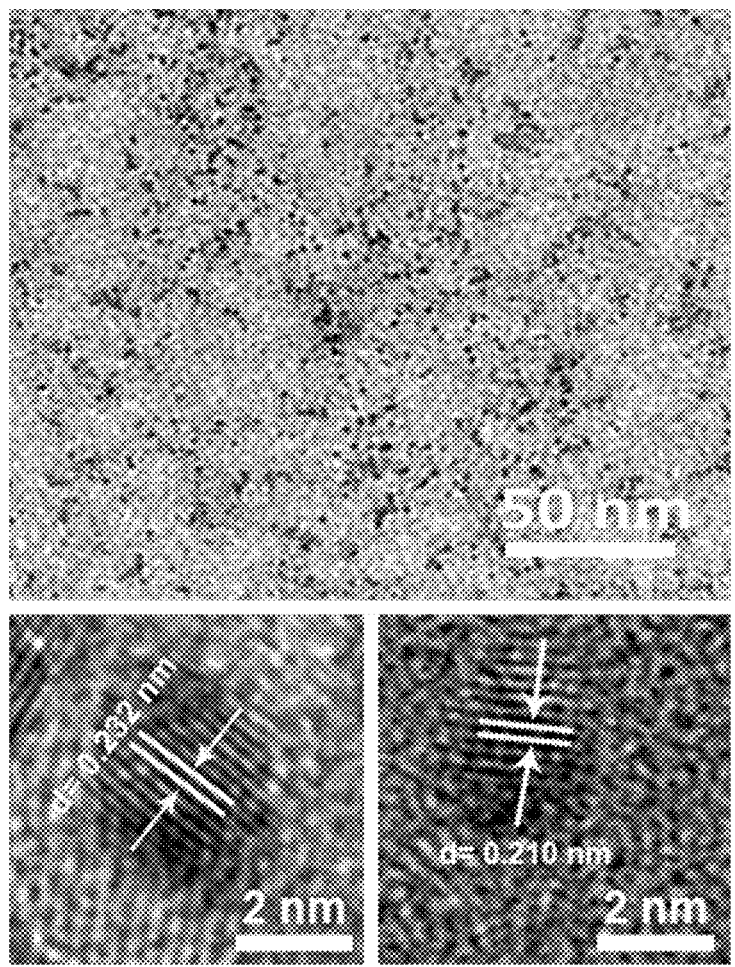
FIG. 4 is an electron micrograph of the cisplatin protein nanoparticles of Example 9.

The steps in this example were the same as those of Example 1, except that potassium chloride (KCl) aqueous solution was added as the ligand ion, chloride ions, to prepare cisplatin protein nanoparticles. The prepared nanoparticles were photographed by electron microscopy. The result is shown in FIG. 4. As shown (the two small images below are high-resolution electron micrographs), the average particle size of the prepared nanoparticles is 3.7±0.1 nm.

Example 10

The steps in this example were the same as those of Example 1, except that potassium bromide (KBr) was added as the ligand ion, bromide ions, to prepare bromoplatinum protein nanoparticles. The average particle size of the prepared nanoparticles is 4.7±0.2 nm.

Example 11

The steps in this example were the same as those of Example 1, except that sodium 1,1-cyclobutane dicarboxylate was added as ligand ion, 1,1-cyclobutane dicarboxylate ion, to prepare carboplatin protein nanoparticles. The particle size is 2.4±0.2 nm.

Example 12

The steps in this example are the same as those of Example 1, except that sodium glycolate was added as the ligand ion, glycolate ions, to prepare nedaplatin platinum protein nanoparticles. The average particle size is 2.3±0.4 nm.

Example 13

The steps in this embodiment are the same as those in the first embodiment. The difference is that sodium bicarbonate is added to introduce the ligand ion carbonate ions to prepare platinum carbonate protein nanoparticles with an average particle size of 6.5±0.5 nm.

Example 14

The steps in this example were the same as those of Example 1, except that bovine serum albumin (BSA) solution was used as the protein solution to prepare iodoplatin BSA-encapsulated protein nanoparticles. The average particle size is 6.1±1.2 nm.

Example 15

The steps in this example were the same as those in Example 1, except that human transferrin (Trf) solution was used as the protein solution to prepare iodoplatin transferrin nanoparticles. The average particle size is 5.5±0.9 nm.

Example 16

The steps in this example were the same as those of Example 1, except that with oxaliplatin was used instead of cisplatin to prepare iodoplatin protein nanoparticles. The average particle size is 6.8±0.8 nm.

Example 17

The steps in this example were the same as those of Example 1, except that carboplatin was used instead of cisplatin to prepare iodoplatin protein nanoparticles. The average particle size is 7.2±0.8 nm.

Example 18

The steps in this example were the same as those of Example 1, except that silver sulfate was substituted for silver nitrate to prepare iodoplatinum protein nanoparticles. The average particle size of which is 7.0±1.0 nm.

Comparative Examples

The steps were the same as those of Example 1, except that the molar ratio of platinum prodrug compound to the ligand ion was 1:0.3, and the rest of the process remained the same. Nanoparticles were made.

The steps were the same as those of Example 1, except that the concentration of the human serum albumin (HSA) solution was 2.0 mg/mL (the molar ratio of the platinum prodrug compound to the human serum albumin was 100:1). The solution produced yellow precipitation. Nanoparticles were not made.

The steps were the same as those of Example 1, except that the concentration of the human serum albumin (HSA) solution remained unchanged, and the molar ratio of platinum prodrug compound to human serum albumin was 500:1. The solution produced yellow precipitate. Nanoparticles were not made.

The steps were the same as those of Example 1, except that respectively take the saturated aqueous solution of platinum drugs (such as cisplatin, oxaliplatin, carboplatin or nedaplatin) and thoroughly mix the 13.3 mg/mL human serum albumin (HSA) aqueous solution (The molar ratio of platinum drugs to human serum albumin is 100:1), adjust the pH of the mixed solution to 6.4 with 0.2 M NaOH solution, then heat the reaction at 55° C. for 4 hours, and then add the resulting mixture to the ultrafiltration tube After centrifugation at 2000 rpm, nanoparticles could not be produced.

Figure 5:
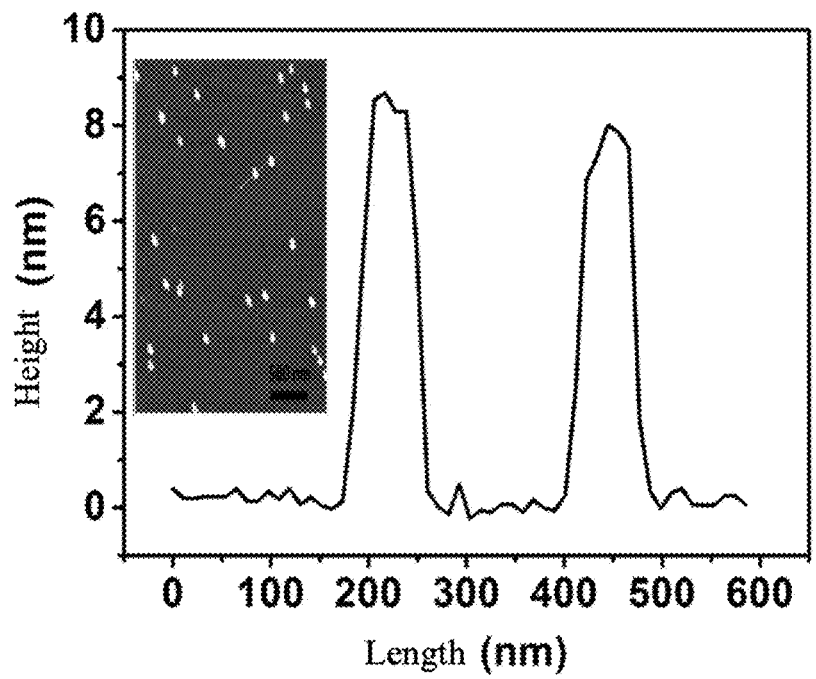
FIG. 5 is an atomic force microscope of the iodoplatin protein nanoparticles of Example 1.
Figure 6:
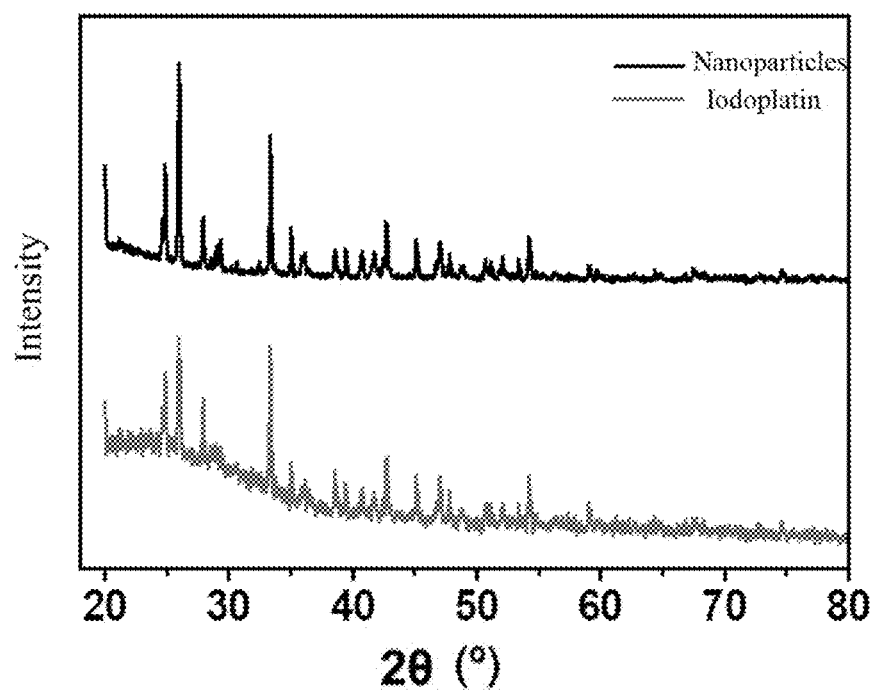
FIG. 6 is an X-ray diffraction pattern of the iodoplatin protein nanoparticles of Example 1.
Figure 7:
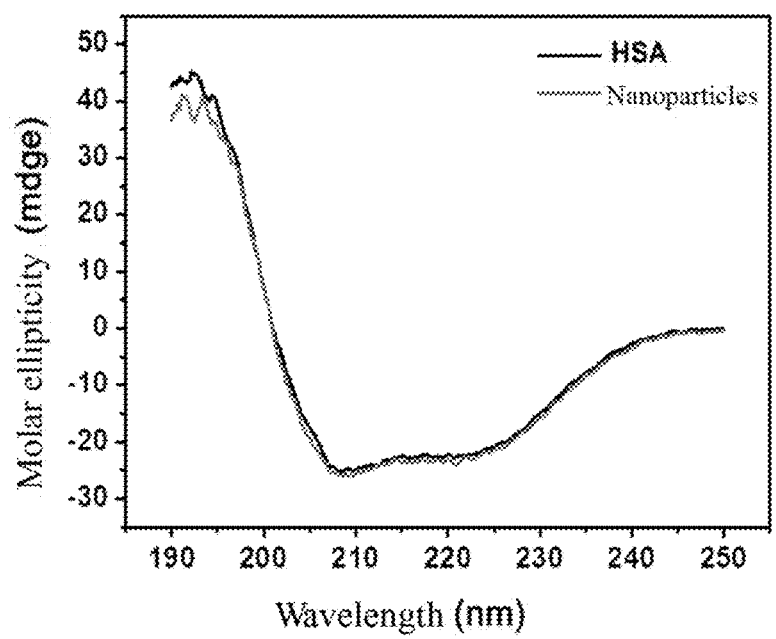
FIG. 7 is a circular dichroism spectrum of the iodoplatin protein nanoparticles of Example 1.

The property and activity tests of the platinum drug mineralized protein nanoparticles prepared in the examples are as follows:

1. The physical structure of the iodoplatin protein nanoparticles prepared in Example 1: The specific steps: atomic force microscopy (AFM) imaging, X-ray diffraction (XRD), and circular column chromatography (CD) were performed on the prepared iodoplatin protein nanoparticles. The AFM spectrum (FIG. 5) shows that the prepared protein nanoparticles are uniformly dispersed and uniform in shape and size; XRD results (FIG. 6) show that the iodoplatin nanocrystals in the iodoplatin protein nanoparticles are consistent with the free iodoplatin crystal form, which indicates that the iodoplatin nanoparticles crystals grow in the protein cavity; CD results (FIG. 7) show that the albumin loaded with iodoplatin nanocrystals has no significant difference from the blank HSA curve of the control group, which indicates that the secondary structure of albumin is not destroyed during the preparation of the nanoparticles.

Figure 8:
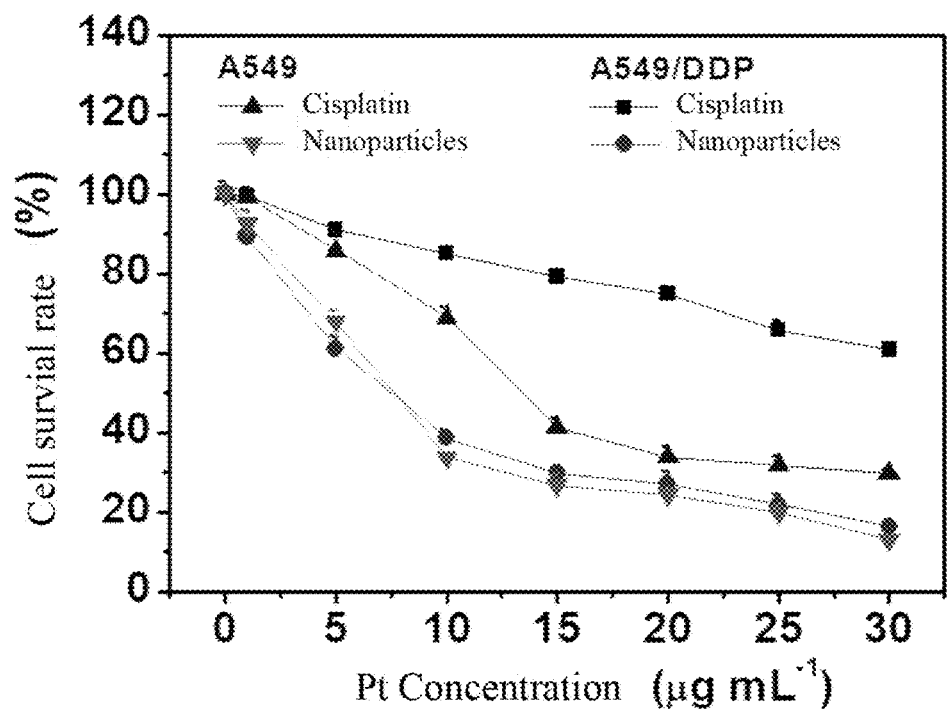
FIG. 8 is a graph showing the cytotoxicity of the iodoplatin protein nanoparticles prepared in Example 1 of the present invention and free cisplatin on the cell survival rate of the A549 cell line and the A549/DDP cisplatin-resistant cell line (cisplatin (DDP))

2. The cytotoxicity of the iodoplatin protein nanoparticles prepared in Example 1: The specific steps: taking A549 and cisplatin-resistant strain A549/DDP cells in logarithmic growth phase and seeding on a 96-well plate with a seeding density of $6\times10^3$/mL, 100 μL per well. Placing the plate in a cell incubator for 12 hours at constant temperature. After confirming that the cells adhere to the wall, discard the culture solution, wash 1-2 times with phosphate buffer, and add iodoplatin protein nanoparticles that were dissolved in the medium, 100 microliters per well, the nanoparticle concentration gradient was 1, 5, 10, 15, 20, 25 μg/mL, 4 replicate wells for each concentration, and the same concentration of cisplatin solution was prepared as a control group. After 24 hours in the incubator, replace the culture medium, add 10 μL of MTT (3-(4,5-dimethylthiazol-2-yl)-2,5-diphenyltetrazolium bromide) PBS (phosphate-buffered saline) solution with a concentration of 5 mg/mL, discard the culture medium after 4 hours, add 200 μL of DMSO (dimethylsulfoxide), shake for 10 minutes, measure the absorbance value at 490 nm with a microplate reader. The results (FIG. 8) show that the $IC_{50}$ values of the nanoparticles on the A549 cell line and the A549/DDP resistant strain were 6.9 μg/ml and 6.8 μg/ml, respectively, while the free cisplatin was less cytotoxic to the resistant cells. It indicates that the protein nanoparticles of the invention can effectively overcome the resistance of A549/DDP.

Figure 9:
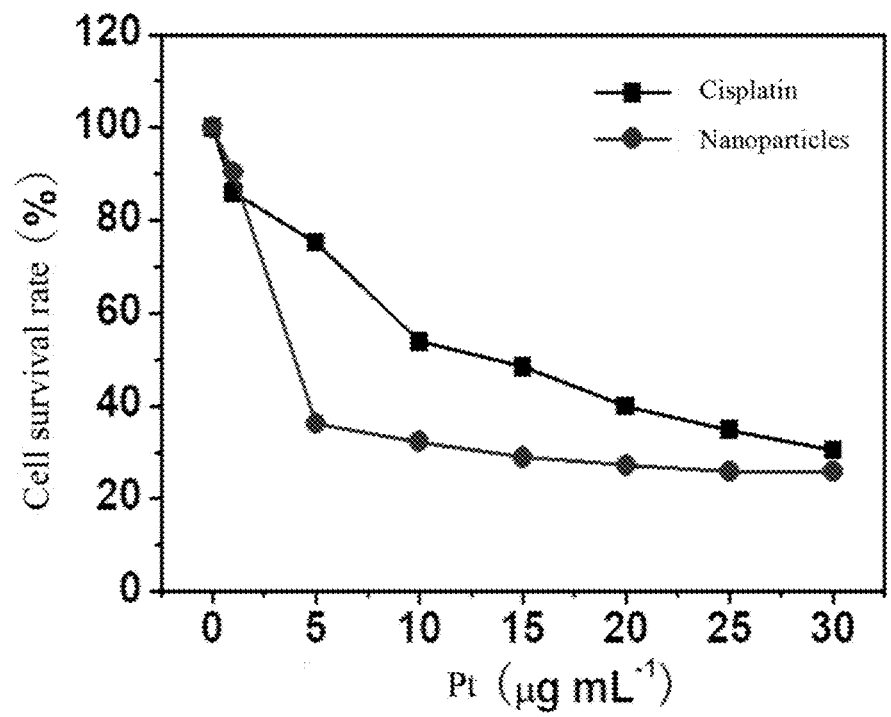
FIG. 9 is a graph showing the cytotoxicity of the iodoplatin protein nanoparticles prepared in Example 1 of the present invention and free cisplatin on the cell survival rate of HepG-2 (a human hepatoma-derived cell line) cell lines.

3. The cytotoxicity of the iodoplatin protein nanoparticles prepared in Example 1 on the natural non-sensitive cisplatin cell line HepG-2: HepG2 cells in the logarithmic growth phase were seeded in a 96-well plate with a seeding density of $1\times10^5$ cells/mL, 100 μL per well, and the rest of the steps were the same as above. The results are shown in FIG. 9. It can be seen that the $IC_{50}$ of the nanoparticle for HepG-2 cell line is 4.5 μg/ml, while the $IC_{50}$ of free cisplatin is 12.6 μg/ml, indicating that the protein nanoparticles of the present invention have strong cytotoxic effect on the natural non-sensitive cell line HepG-2 of cisplatin. The lyophilized powder of iodoplatin protein nanoparticles in Example 1 was reconstituted with water and subjected to the same test, and the $IC_{50}$ for the HepG-2 cell line was 4.6 μg/mL.

Figure 10:
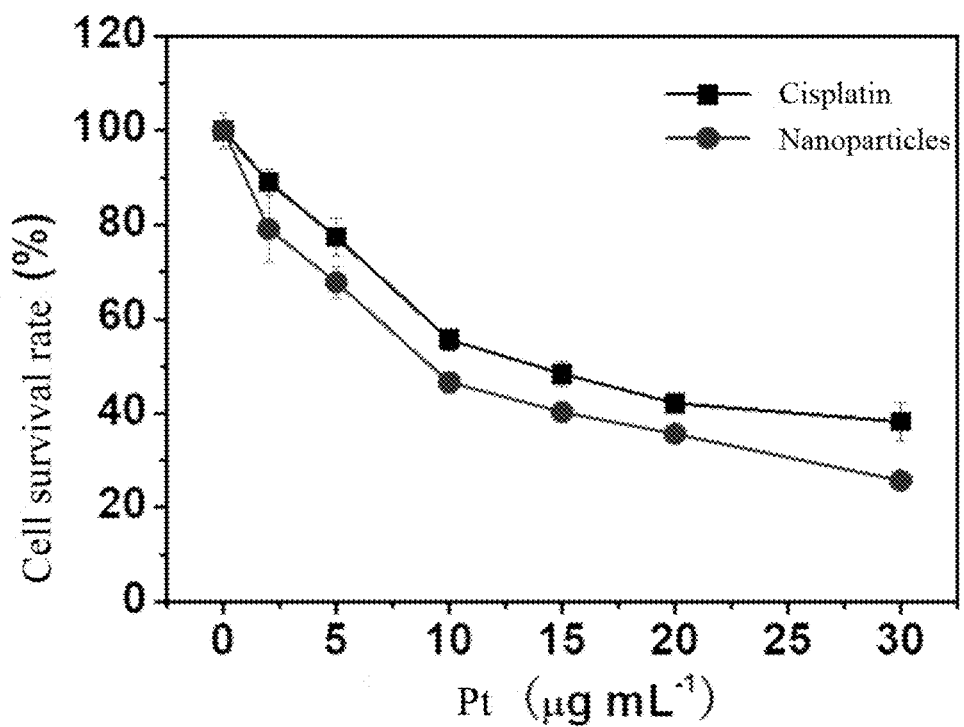
FIG. 10 is a graph showing the cytotoxicity of cisplatin protein nanoparticles prepared in Example 9 of the present invention and free cisplatin on the cell survival rate of the A549 cell line.

4. The cytotoxicity test of the cisplatin protein nanoparticles prepared in Example 9: The specific steps: take the A549 in the logarithmic growth phase at an inoculation density of $6\times10^3$ pcs/mL, 100 μL per well, and place it in a cell incubator at constant temperature culture for 12 hours. After confirming that the cells adhere to the wall, discard the culture medium, wash 1-2 times with phosphate buffer, and add the cisplatin protein nanoparticle solution prepared with the medium, 100 μL per well, and the concentration gradient of nanoparticles was 2, 5, 10, 15, 20, 30 μg/ml, 4 replicate holes for each concentration, and at the same time prepare the same concentration of cisplatin solution as the control group. After 24 hours in the incubator, replace the culture medium and add 10 μL PBS solution with a MTT concentration of 5 mg/mL. The culture medium was discarded after 4 hours, 200 μL of DMSO was added, and the mixture was shaken for 10 minutes. The absorbance at 490 nm was measured by the microplate reader. The results (FIG. 10) show that the $IC_{50}$ of the nanoparticle group is about half of the $IC_{50}$ of the cisplatin group.

Figure 11:
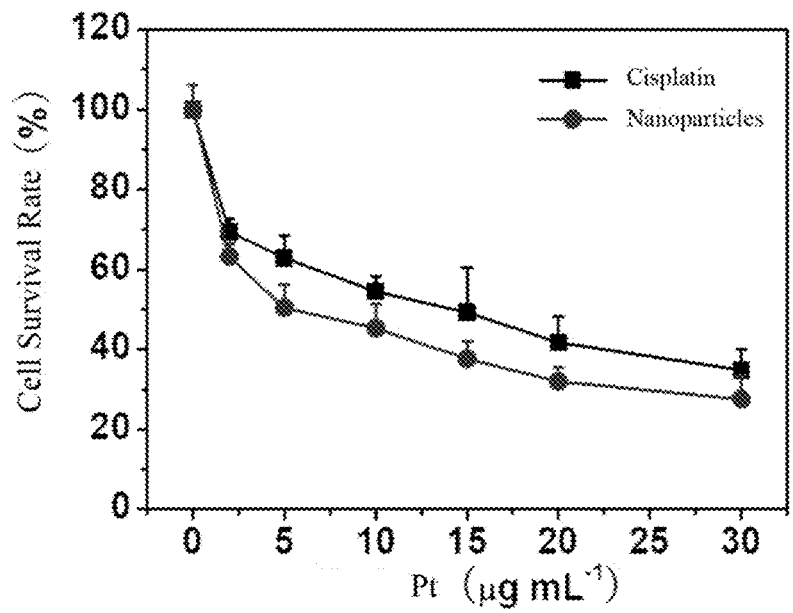
FIG. 11 is a graph showing the cytotoxicity of the iodoplatin transferrin nanoparticles prepared in Example 15 of the present invention and free cisplatin on the cell survival rate of A549 cell line.

5. The cytotoxicity of the iodoplatin transferrin nanoparticles prepared in Example 15: the specific steps: take the A549 in the logarithmic growth phase at an inoculation density of 6×103 cells/mL, 100 μL per well, and place it in a cell incubator at constant temperature culture for 12 hours. After confirming that the cells adhere to the wall, discard the culture solution, wash 1-2 times with phosphate buffer, and add the iodoplatin transferrin nanoparticle solution prepared with the culture medium, 100 μL per well. The particle concentration gradient was 2, 5, 10, 15, 20, 30 μg/mL, 4 replicate holes for each concentration, and the same concentration of cisplatin solution was prepared as a control group. After 24 hours of culture in the incubator, change the culture, add 10 μL of 5 mg/mL MTT in PBS. After 4 hours, discard the culture solution, add 200 μL of DMSO, shake for 10 minutes, and measure the absorbance at 490 nm with a microplate reader. FIG. 11 shows that the $IC_{50}$ of the nanoparticle group is about one third of that of the cisplatin group.

The platinum drug mineralized protein nanoparticles were added to physiological saline to prepare tumor treatment drugs for the following analysis.

Figure 12:
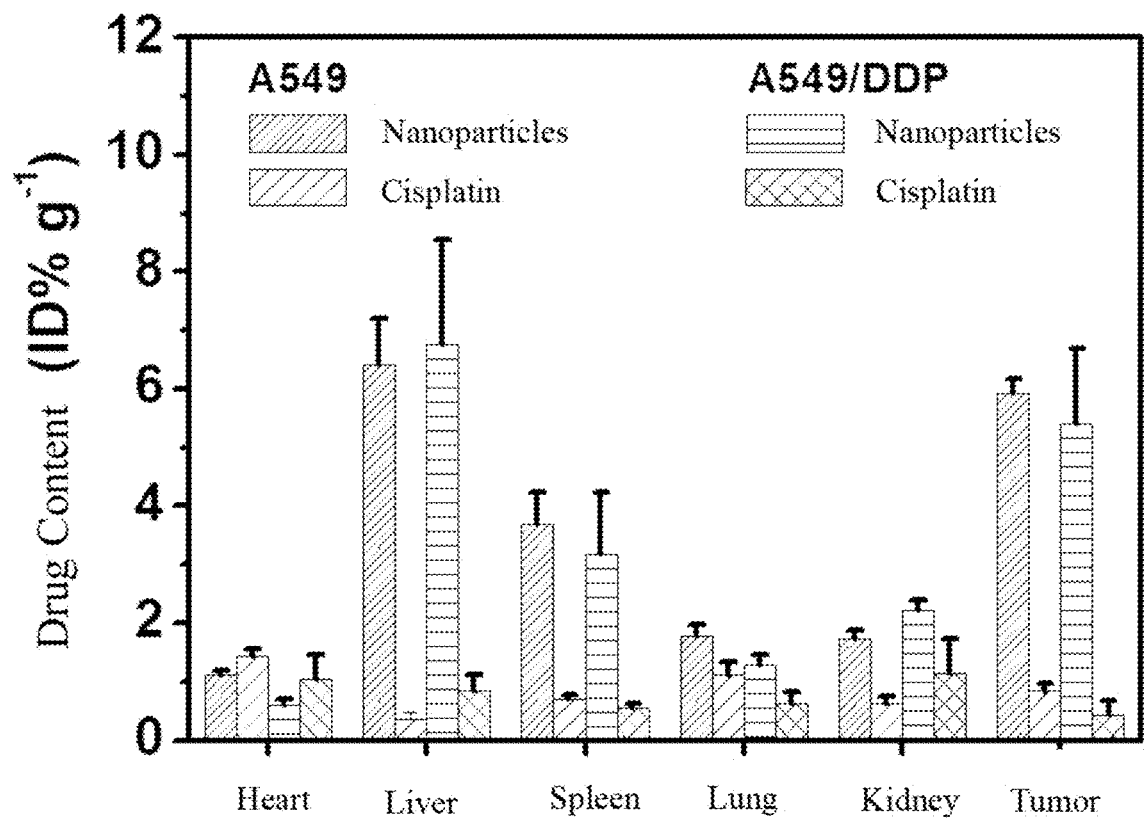
FIG. 12 is the tissue distribution result of iodoplatin protein nanoparticles prepared in Example 1 of the present invention in tumor-bearing nude mice.

6. The tissue distribution experiment in mice was performed on the nanoparticles prepared in Example 1: The specific experiment steps were as follows:
   (1) Tumor model establishment: culture A549 and A549/DDP tumor cells, digest them to prepare a cell suspension of $1\times10^7$ cells/mL to ensure uniform dispersion of cells, inoculate tumors under the armpits of nude mice, and inject 150 subcutaneously into each mouse μL, observe the size of the tumor every day. Tumor volume formula:

Tumor volume=(length×width$^2$)/2;

(2) The nanoparticles of Example 1 were injected into two groups of tumor-bearing nude mice (platinum administration dose is 1 mg/kg) through the tail vein, and the heart, liver, spleen, lung, and kidney of the three groups of nude mice were taken out 24 hours after the injection. Aqua regia was used to digest the tissue at high temperature. After the tissue was digested, the volume was adjusted to 10.0 mL. After filtering with a 0.22 micron microporous membrane, the platinum element in each tissue is quantified by ICP-OES (Inductively Coupled Plasma Optical Emission Spectroscopy). The distribution results of platinum content in various tissues of nude mice were obtained by the above measurement method (FIG. 12). It can be seen from the figure that the nanoparticles of the present invention have good tumor targeting properties for both the A549 tumor model and the A549/DDP tumor model.

Figure 13:
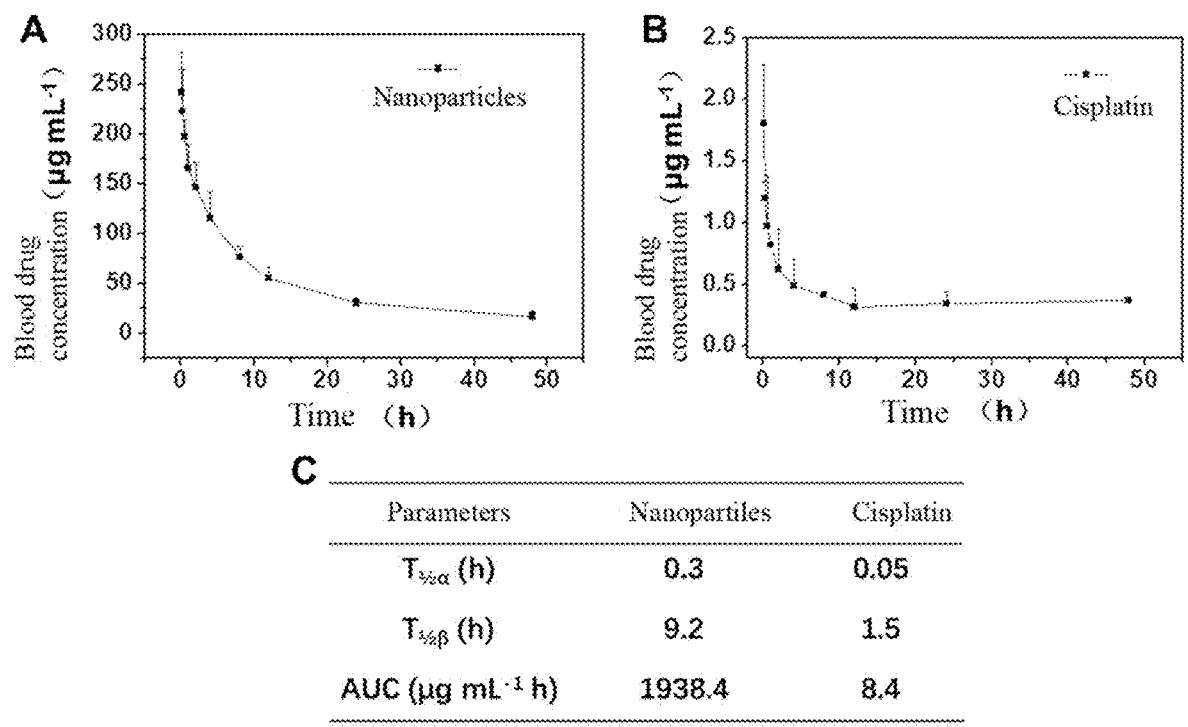
FIG. 13 shows the pharmacokinetic results of iodoplatin protein nanoparticles and cisplatin, where A is the pharmacokinetic curve of iodoplatin nanoparticles, B is the pharmacokinetic curve of free cisplatin, and C is the pharmacokinetic parameter.

7. Pharmacokinetic test:

Investigate the blood drug concentration of the iodoplatin protein nanoparticles of Example 1: Take an appropriate number of mice and divide them into seven groups, each for 0, 2, 4, 6, 8, 12, 24, and 48 hours. Take blood samples at time point, three in each group in parallel. The dose of platinum administered to each mouse was 1 mg/kg. When the administration time reached the above-mentioned time point, the mouse blood samples were taken. The blood samples were dissolved in aqua regia and perchloric acid solution and burned at high temperature. The residue was dissolved in 5 mL of water and treated with a 0.22 micron microporous filter membrane. The platinum element in each tissue was quantified by ICP-OES, and the curve in FIG. 13 was obtained, indicating that the nanoparticles have a very good long-body circulation effect.

Figure 14:
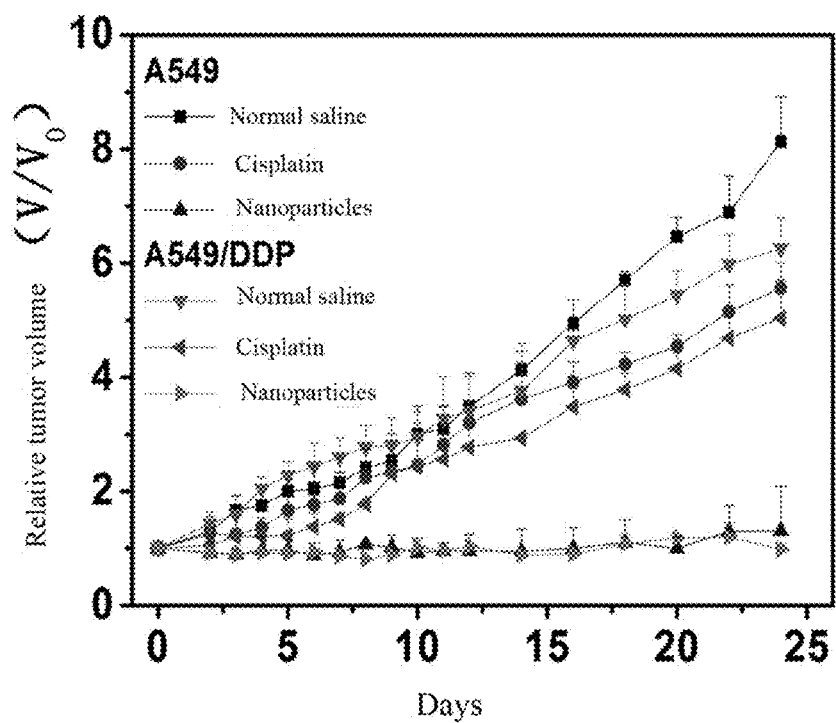
FIG. 14 is a graph showing the tumor inhibition curve of iodoplatin protein nanoparticles prepared in Example 1 of the present invention on lung tumor model tumor-bearing nude mice within 25 days.

8. The iodoplatin protein nanoparticles of Example 1 were investigated for the anti-tumor effect of lung cancer in nude mice: the tumor model established above was used to construct a nude mouse tumor-bearing model. When the tumor volume reached 50-80 mm$^3$, the administration was designed as follows: the iodoplatin protein nanoparticles of Example 1 group (platinum administration dose was 1 mg/kg), free cisplatin group (platinum administration dose was 1 mg/kg), physiological saline group, 5 in each group, administering once every 5 days. It can be seen from the effect of tumor changes in nude mice in FIG. 14 that the injection of physiological saline group has no effect on the growth of the tumors of the A549 tumor model and the A549/DDP tumor model, while the injection of nanoparticles group has significant inhibition on the growth of the two tumor models. During the observation period, the nude mice were in good condition and did not die, indicating that the protein nanoparticles of the present invention can effectively inhibit the growth of drug-resistant tumors; at the same time, the free cisplatin group also has a certain tumor-inhibiting effect on the two tumor models, but during the observation period, the nude mice were in poor condition and lost weight.

Figure 15:
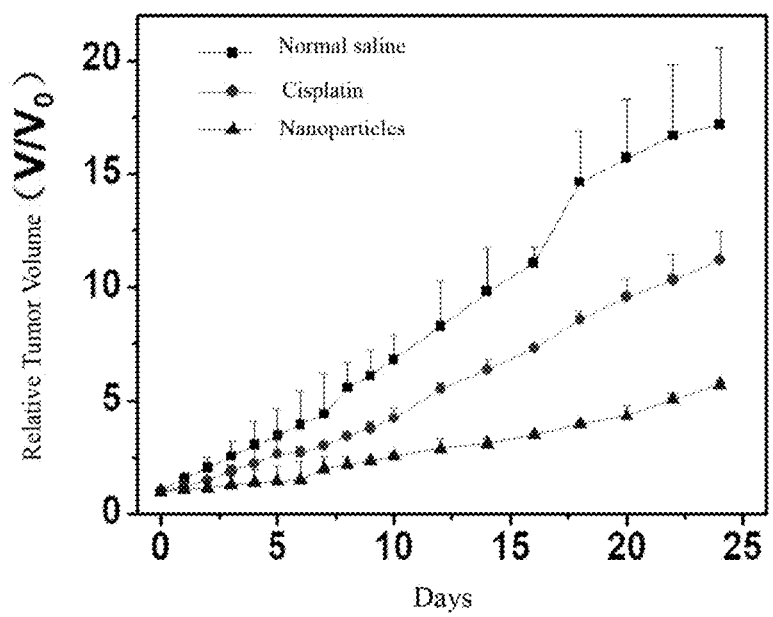
FIG. 15 is a graph showing the tumor inhibition curve of iodoplatin protein nanoparticles prepared in Example 1 of the present invention on tumor-bearing nude mice of liver tumor model within 25 days.

9. The iodoplatin protein nanoparticles prepared in Example 1 were investigated for the anti-tumor effect of liver tumors in nude mice: the establishment of tumor model: HepG2 tumor cells were cultured and digested to prepare 1×10$^7$ cells/mL cell suspension to ensure the cells were evenly dispersed, and tumors were planted in the armpits of nude mice. Each mouse was injected with 150 μL subcutaneously, and the tumor volume was observed every day. When the tumor volume reaches 50-80 mm$^3$, the drug was administered according to the following design: iodoplatin protein nanoparticles group (platinum dose was 1 mg/kg), free cisplatin group (platinum dose was 1 mg/kg), physiological saline Group, 5 animals in each group, administering once every 5 days. It can be seen from the effect of tumor changes in nude mice in FIG. 15 that the normal saline injection group has no effect on the growth of the HepG2 tumor model tumor, while the nanoparticle injection group has an inhibitory effect on the growth of the tumor model. The nude mice were in good condition during the observation period. The absence of death indicates that the protein nanoparticles of the present invention can also effectively inhibit the growth of HepG2 tumors.

Figure 16:
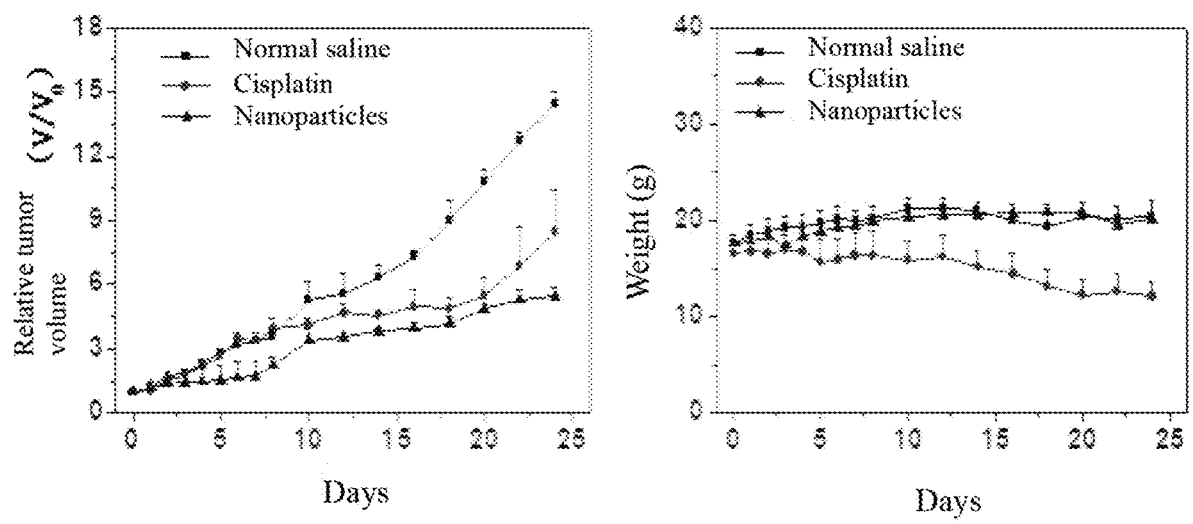
FIG. 16 shows the antitumor effect and body weight changes of iodoplatin protein nanoparticles prepared in Example 1 of the present invention on breast cancer model tumor-bearing mice.

10. The iodoplatin protein nanoparticles prepared in Example 1 were investigated for the anti-tumor effect of breast cancer in mice: the establishment of tumor model: 4T1 tumor cells were cultured and digested to prepare 1×10$^7$ cells/mL cell suspension to ensure the cells were evenly dispersed. 50 μL of cell suspension was subcutaneously injected into the right leg muscle of Balb/c female mice, and the tumor volume was observed every day. When the tumor volume reached 50-80 mm$^3$, the drug was administered according to the following design: iodoplatin protein nanoparticle group (platinum dose was 1 mg/kg), free cisplatin group (platinum dose was 1 mg/kg), physiological saline Group, 5 animals in each group, administering once every 5 days. It can be seen from the effect of tumor changes in FIG. 16 that the normal saline injection group has no effect on the growth of the 4T1 tumor model tumor, while the nanoparticle injection group has an inhibitory effect on the growth of the tumor model. The nude mice were in good condition during the observation period. The absence of death indicates that the protein nanoparticles of the present invention can effectively inhibit the growth of 4T1 tumors.

Figure 17:
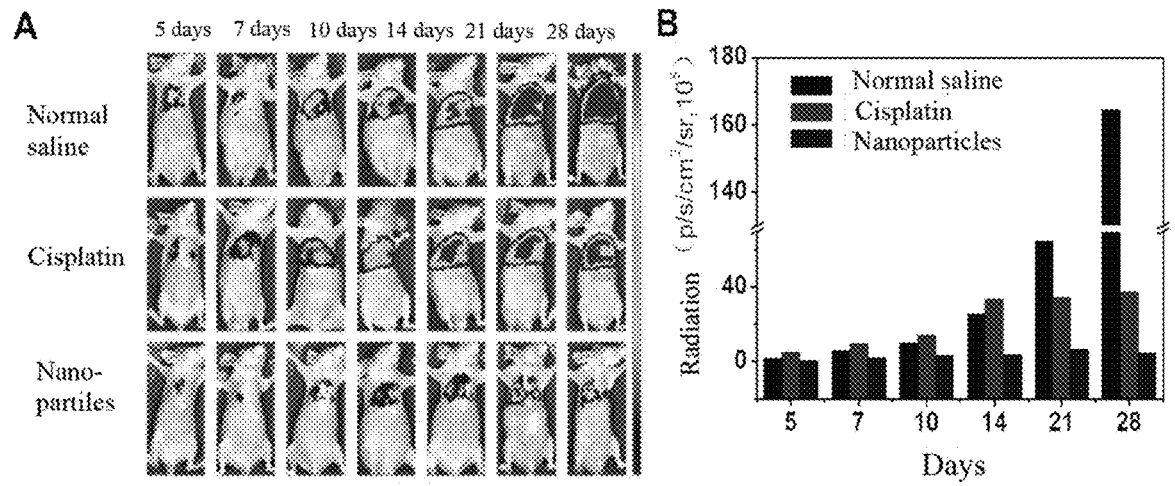
FIG. 17 shows the anti-tumor effect of iodoplatin protein nanoparticles on lung tumors in nude mice, where A is the fluorescence imaging images of normal saline, free cisplatin, and iodoplatin nanoparticles at different times, and B is the fluorescence intensity change of tumor tissue.

11. The iodoplatin protein nanoparticles prepared in Example 1 were investigated for the anti-tumor effect of lung cancer in mice: the establishment of tumor model: A549-luc tumor cells were cultured and digested to prepare 1×10$^7$ cells/mL cell suspension. Inject 150 μL of cell suspension into the lungs of nude mice, and intraperitoneally inject fluorescein sodium salt (15 mg/ml, 200 μL) into the lungs of nude mice. Observe the tumor growth under the small animal imager. When the fluorescence intensity of the tumor in the lung reached 50000 p/s/cm$^2$/sr, the drug was administered according to the following design: iodoplatin protein nanoparticle group (platinum dose was 1 mg/kg), free cisplatin group (platinum dose as 1 mg/kg), normal saline group, 5 mice in each group, administering once every 5 days. It can be seen from the changes in fluorescence intensity at tumor sites of mice in FIG. 17 that the tumor growth of the A549-luc orthotopic tumor model in the saline injection group was not affected, while the tumor growth in the iodoplatin nanoparticle group was significantly inhibited. During the observation period, the nude mice were in good condition and did not die, indicating that the protein nanoparticles of the present invention can effectively inhibit the growth of A549-luc tumors.

Figure 18:
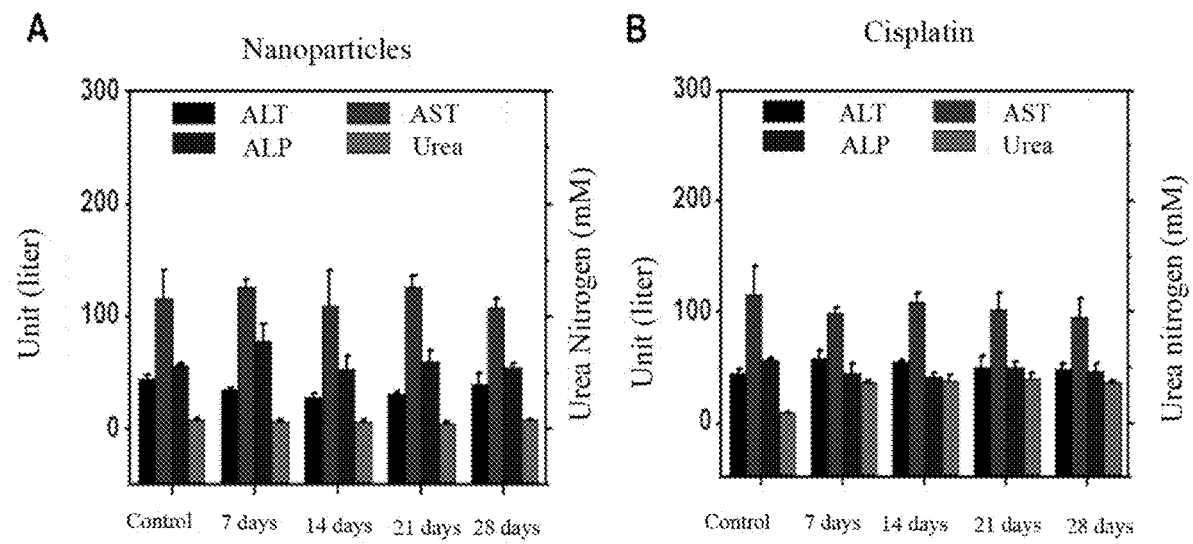
FIG. 18 shows the serum levels of alanine aminotransferase (ALT), aspartate aminotransferase (AST), alkaline phosphatase (ALP) and urea nitrogen (Urea) after treatment with iodoplatin protein nanoparticles and cisplatin, where A and B are the experimental results of iodoplatin nanoparticles and free cisplatin, respectively.

12. To investigate the plasma concentration of the iodoplatin protein nanoparticles and free cisplatin described in Example 1: Take normal female Balb/c mice and divide them into (1) PBS group and (2) 7-day group after drug injection, (3) 14-day group, (4) 21-day group, (5) 28-day group, 3 in each group. Each mouse was administered via the tail vein (1 mg/mL, once every 5 days). After a total of 5 administrations for 25 days, each mouse was taken by eyeball blood sampling at 7, 14, 21, and 28 days after administration. A 0.5 mL blood sample from a mouse was placed overnight at 4° C. and centrifuged at 1000 rpm for 5 min. The upper clarified serum 200 μL was taken out to measure the alanine aminotransferase (ALT), aspartate aminotransferase (AST), alkaline phosphatase (ALP) and urea nitrogen (Urea) contents. The results are shown in FIG. 18. 7 days after complete injection of the drug, the urea nitrogen content of the cisplatin group was significantly different from that of the control group, indicating that cisplatin has certain kidney damage to the mice.

Figure 19:
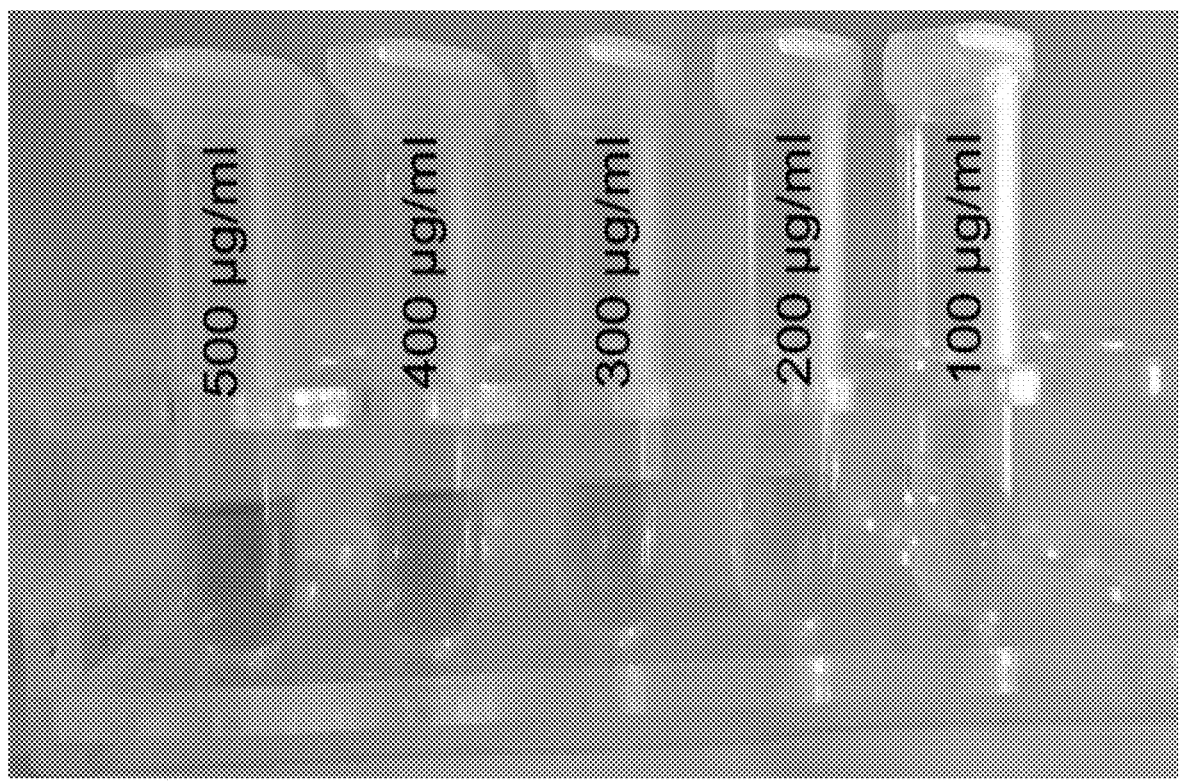
FIG. 19 is a photograph of the aqueous solution of iodoplatin protein nanoparticles of Example 1, where the number indicates the concentration of platinum iodide.

FIG. 19 is a photograph of the iodoplatin protein nanoparticles aqueous solution of Example 1, where the number represents the concentration of platinum iodide, indicating that the nanoparticles obtained in the present invention are very water-soluble.

The invention claimed is:

1. Anti-tumor platinum drug mineralized protein nanoparticles, wherein the anti-tumor platinum drug mineralized protein nanoparticles comprise a platinum drug and a protein,
    wherein the protein is selected from the group consisting of albumin, transferrin, hemoglobin, and lipoprotein; and the platinum drug is selected from the group consisting of cisplatin, iodoplatinum, bromoplatinum, oxaliplatin, carboplatin, and nedaplatin; and
    wherein the platinum drug is contained in inner cavity of the protein, and wherein a mass ratio of the platinum drug-to-(the platinum drug and the protein) is in the range of 1%-50%.

2. A method for preparing anti-tumor platinum drug mineralized protein nanoparticles, wherein the method comprises the following steps:
    (1) reacting a platinum drug and a silver salt in water and removing a precipitate to obtain a platinum prodrug compound aqueous solution; then mixing the platinum prodrug compound aqueous solution and a protein aqueous solution to obtain a platinum prodrug compound and protein complex mixture, the protein aqueous solution comprising a protein;
    (2) adjusting a pH value of the platinum prodrug compound and protein complex mixture to 4-12, adding a ligand aqueous solution, purifying and lyophilizing to obtain the platinum drug mineralized protein nanoparticles,
    wherein the protein is selected from the group consisting of albumin, transferrin, hemoglobin, and lipoprotein; and the platinum drug is selected from the group consisting of cisplatin, iodoplatinum, bromoplatinum, oxaliplatin, carboplatin, and nedaplatin; and
    wherein the platinum drug is contained in a cavity of the protein to achieve controllable growth of a particle size of the platinum drug and to obtain a mineralization of the platinum drug.

3. The method for preparing anti-tumor platinum drug mineralized protein nanoparticles according to claim 2, wherein, in step (1), a centrifugal separation is used to remove the precipitate, and the reaction between the platinum drug and the silver salt is conducted at 50-60° C. in absence of light for 3 hours, and then at room temperature for 10-12 hours; and in step (2), purifying is a centrifugal treatment in an ultrafiltration tube.

4. The method for preparing anti-tumor platinum drug mineralized protein nanoparticles according to claim 2, wherein a molar ratio of the platinum drug to the silver salt is from 1:1 to 5:1; a molar ratio of the platinum prodrug compound to the protein is from 20:1 to 200:1; a molar ratio of the platinum prodrug compound to the ligand is from 1:1 to 1:16; and a concentration of the protein in the protein aqueous solution is 1-25 mg/mL.

5. The method for preparing anti-tumor platinum drug mineralized protein nanoparticles according to claim 4, wherein the molar ratio of the platinum drug to the silver salt is from 2:1 to 4:1; the molar ratio of the platinum prodrug compound to the protein is from 50:1 to 150:1; the molar ratio of the platinum prodrug compound to the ligand is from 1:4 to 1:12; and the concentration of the protein in the protein aqueous solution is 3-20 mg/mL.

6. The method for preparing anti-tumor platinum drug mineralized protein nanoparticles according to claim 2, wherein the ligand is selected from the group consisting of potassium chloride, potassium bromide, potassium iodide, 1,1-cyclobutane dicarboxylate, glycolate, oxalate, carbonate, and bicarbonate; and wherein the silver salt is silver nitrate or silver sulfate.

7. An anti-tumor platinum drug mineralized protein nanoparticles freeze-dried powder, wherein a method of preparing the anti-tumor platinum drug mineralized protein nanoparticles freeze-dried powder comprises the following steps:
    (1) reacting a platinum drug and a silver salt in water and removing a precipitate to obtain a platinum prodrug compound aqueous solution; then mixing the platinum prodrug compound aqueous solution and an aqueous protein solution to obtain a platinum prodrug compound and protein complex mixture, the protein aqueous solution comprising a protein;
    (2) adjusting a pH value of the platinum prodrug compound and protein complex mixture to 4-12, adding an aqueous ligand solution, purifying, and lyophilizing to obtain the anti-tumor platinum drug mineralized protein nanoparticles freeze-dried powder,
    wherein the protein is selected from the group consisting of albumin, transferrin, hemoglobin, and lipoprotein; and the platinum drug is selected from the group consisting of cisplatin, iodoplatinum, bromoplatinum, oxaliplatin, carboplatin, and nedaplatin; and
    wherein the platinum drug is contained in a cavity of the protein to achieve controllable growth of a particle size of the platinum drug and to obtain a mineralization of the platinum drug.

* * * * *